United States Patent [19]

Saulson et al.

[11] 4,416,282
[45] Nov. 22, 1983

[54] CARDIAC PACER WITH IMPROVED, OUTPUT CIRCUITRY

[75] Inventors: Stanley H. Saulson; Peter P. Tarjan, both of Miami, Fla.

[73] Assignee: Cordis Corporation, Miami, Fla.

[21] Appl. No.: 239,468

[22] Filed: Mar. 2, 1981

[51] Int. Cl.³ .............................................. A61N 1/36
[52] U.S. Cl. ............................................. 128/419 PG
[58] Field of Search ................. 128/419 PG, 421, 422

[56] References Cited

U.S. PATENT DOCUMENTS

| | | | |
|---|---|---|---|
| 3,631,860 | 1/1972 | Lopin | 128/419 PG |
| 3,746,005 | 7/1973 | Thaler et al. | 128/419 PG |
| 3,851,651 | 12/1974 | Icenbice, Jr. | 128/422 |
| 3,945,387 | 3/1976 | Adams | 128/419 PG |
| 4,049,004 | 9/1977 | Walters | 128/419 PG |

*Primary Examiner*—William E. Kamm
*Attorney, Agent, or Firm*—Kenway & Jenney

[57] ABSTRACT

A fully implantable programmable cardiac pacer includes two main pacing channels driven by a crystal oscillator circuit. For each channel, amplitude and pulse width are programmed in paired combinations corresponding to monotonically increasing charge density. Selectively combinable constant current sources are shared by each channel. A low battery indicator system samples battery voltage relative to two threshold levels. In magnet rate, if the main battery voltage is above the first threshold, the fixed pacer output will be 70 beats per minute. If the battery voltage is between the first and second threshold levels, the fixed pacer output will be 62.5 beats per minute. An emergency RC oscillator continuously produces an output at 52.5 beats per minute and one millisecond pulse width. The emergency output is switched directly to the output of channel 2 when either the low battery voltage falls below the second threshold or the crystal oscillator frequency changes when tested by a frequency checking circuit using the output of the RC oscillator as a reference clock. An emergency battery is coupled to the main battery via a diode steering circuit which allows the remaining capacity to be combined with that of the emergency battery.

4 Claims, 8 Drawing Figures

CARDIAC PACER WITH IMPROVED OUTPUT CIRCUITRY

BACKGROUND OF THE INVENTION

The invention relates generally to the field of cardiac pacers, and in particular to cardiac pacer sub-systems including magnet rate, low battery indication, power supply, emergency modes, output formation circuits and output programming.

The physical characteristics of the human heart lend themselves to various interactive artificial pacing systems. There are two major pumping chambers in the heart, the left and right ventricles. Simultaneously contracting, these chambers expel blood into the aorta and the pulmonary artery. Blood enters the ventricles from the left and right atria, respectively. The atria are small antechambers which contract in a separate action which precedes the major ventricular contraction by an interval of about 100 milliseconds (ms), known as the AV delay. The contractions arise from a wave of electrical excitation which begins in the right atrium and spreads to the left atrium. The excitation then enters the atrioventricular node which delays its passage via the bundle of His into the ventricles.

Appearing in the electrocardiogram, a small signal known as the P-wave accompanies atrial contraction while a much larger signal, known as the QRS complex, with a predominant R-wave, accompanies ventricular contraction. The P and R waves can be very reliably detected as timing signals by electrical leads in contact with the respective heart chambers.

The typical implanted cardiac pacer operates by supplying missing stimulation pulses on a pacing lead attached to the ventricle. The R-wave can be sensed by the same lead. An additional lead contacts the atrium to sense P-waves, if desired. In AV sequential pacers, discussed below, the atrial lead is also used for atrial stimulation.

Cardiac pacers are useful in treating a number of cardiac disorders such as heart block caused by impairment of the ability of the bundle of His to conduct normal excitation from the atrium to the ventricle. The pacer itself is a battery powered, hermetically sealed, completely self-contained electronic device which is implanted in the body at a suitable site such as the shoulder or axillary region within an inch from the surface of the skin. The distal ends of the pacer leads are connected inside the heart to the right atrium and right ventricle and extend through a suitable blood vessel to the pacer. The proximal end of the pacer lead is taken out through an opening in the blood vessel and electrically connected to the pacer. Inside the pacer, the stimulation pulses are formed by a pulse generator. In the past, pulse generators have taken several forms but fall into two general categories: (1) those where the pulse generator consists of an R-C timing circuit and (2) those where oscillations in the output of a high frequency clock (R-C or crystal oscillator) are counted by digital circuitry. In circuits of the second kind, the pulse generator typically comprises a digital counter and logic circuitry for producing an output pulse when a given number of clock pulses is counted and means for resetting the counter in response to spontaneous or stimulated activity. An early example is found in U.S. Pat. No. 3,557,796 to Keller et al assigned to the assignee of the present application. With the miniaturization of stored program data processors, microprocessor cardiac pacer systems have given rise to more complex and yet more flexible counting arrangements. For example, a cardiac period number may be placed into a register which is regularly incremented and tested by software instructions. If the register has been counted up to the programmed number, the software branches to direct the formation of a stimulation pulse, as in "Multi-Mode Microprocessor-Based Programmable Cardiac Pacer" U.S. Patent Application Ser. No. 207,003, filed Nov. 14, 1980 by Leckrone et al, assigned to the assignee of the present application, and incorporated herein by reference in its entirety. In this application as in other AV sequential systems, the output circuits for the two channels, i.e. atrium and ventricle, are separate circuits.

It is extremely important to optimize the level of electrical stimulation. The charge density in the myocardium surrounding the bare electrode at the distal end of the pacer lead determines the muscular reaction. Several factors are known to affect this charge density including the amplitude of the stimulation pulse current, the voltage, the duration of the stimulation or "pulse width", the type of electrode including the area of contact and the resistance of the contacting tissue and electrochemical factors as well as the type of lead system used, i.e. unipolar or bipolar. In unipolar systems, the ground terminal is on the pacer itself while in bipolar systems the end of the pacer lead contains two spaced contacts, one of which would be regarded as ground.

Advances in pacer technology have enabled pulse parameters such as rate, width and amplitude to be altered by an externally generated programming signal, for example, using a succession of magnetic pulses to actuate a tiny reed switch in the pacer. In the past, the charge density delivered to the myocardium has been programmable by means of a variable voltage output circuit, a variable constant current output circuit, or a variable pulse width. Once a pacer is implanted and in operation at a selected pulse width and amplitude, it is extremely difficult at a later date for a physician not privy to the current parameter information, to ascertain the exact level of stimulation without knowing the amplitude beforehand. With pacers having fixed (i.e., known) amplitude and variable pulsewidth outputs, one can easily determine the applied stimulation level by gauging the pulsewidth. On the other hand, in providing for a wide range of stimulation levels in a single pacer, it has been found to be more effective to vary the amplitude. However, the stimulation level cannot then be easily determined by superficial electrical measurements.

Cardiac pacers are life-supporting, therapeutic, medical devices. They are surgically implanted and remain within a living person's body for years. The vital considerations in cardiac pacing tend to dictate a conservative approach, if not reluctance, toward commercially exploiting new developments in electronic circuitry. These tendencies are enhanced by the fact that the relatively simple functional requirements of prior art pacers have been easily implemented using pre-existing well-established hardware circuit configurations and also by the state of the art in compact batteries which limits current drain to avoid unnecessary surgical replacements. The chief objective is reliability followed closely by compactness and low current drain.

Two of the critical factors are battery depletion and failure of the main timing circuit. Many systems have been proposed for indicating low battery capacity. In particular, the magnet rate has been used for this purpose before. To observe pacer performance, the physician places a permanent magnet over the pacer which switches the pacer into an asynchronous, i.e. fixed rate, pacing mode in which the pacer's effect on the patient can be easily observed. In the prior art, a low battery indication is provided by sensing the battery voltage and by switching the fixed rate to a substantially different lower rate when a particular battery threshold is reached. See, for example, U.S. Pat. No. 4,095,603 to Davies, assigned to the assignee of the present application, the "Microlith P" Programmable Cardiac Pacer marketed by Cardiac Pacemakers, Inc., and the aforementioned copending application. In a digital pacer, main oscillator failure is difficult to cope with since all the timing for the pacer is based on the nominal frequency of the oscillator output. It is known, however, that when crystal oscillators fail, they usually fail catastrophically and quit vibrating altogether or begin vibrating at multiples of the nominal output frequency.

SUMMARY OF THE INVENTION

Accordingly, the general object of the invention is to provide improved response to low battery condition or main oscillator failure, improved emergency operation and to program the level of stimulation in a manner to cover a wide range of delivered current densities while affording the physician with a simple means for determining the stimulation level by observation. A related object of the invention is to simplify the output formation circuitry by combining several functions.

These and other objects of the invention are achieved in a fully implantable programmable cardiac pacer including two main pacing channels by programming amplitude and pulse width in paired combinations corresponding to monotonically increasing charge density. Selectively combinable constant current sources are shared by each channel. A low battery indicator system samples battery voltage relative to two threshold levels. In magnet rate, if the main battery voltage is above the first threshold, the fixed pacer output will preferably be 70 beats per minute. If the battery voltage is between the first and second threshold levels, the fixed pacer output will preferably be 62.5 beats per minute. An emergency RC oscillator continuously produces an output preferably at 52.5 beats per minute and one millisecond pulse width. The emergency output is switched directly to the output of channel 2 when either the low battery voltage falls below the second threshold or the crystal oscillator frequency changes due to a component failure. The crystal frequency is tested by a frequency checking circuit using the output of the RC oscillator as a reference clock. An emergency battery is coupled to the main battery via a diode steering circuit which allows the remaining capacity to be combined with that of the emergency battery. In addition, the battery voltage powering the pacing logic is isolated from the battery voltage powering the output to minimize the effect of the stimulation pulse on the pacing logic.

DESCRIPTION OF THE PREFERRED EMBODIMENT

Figure 1:
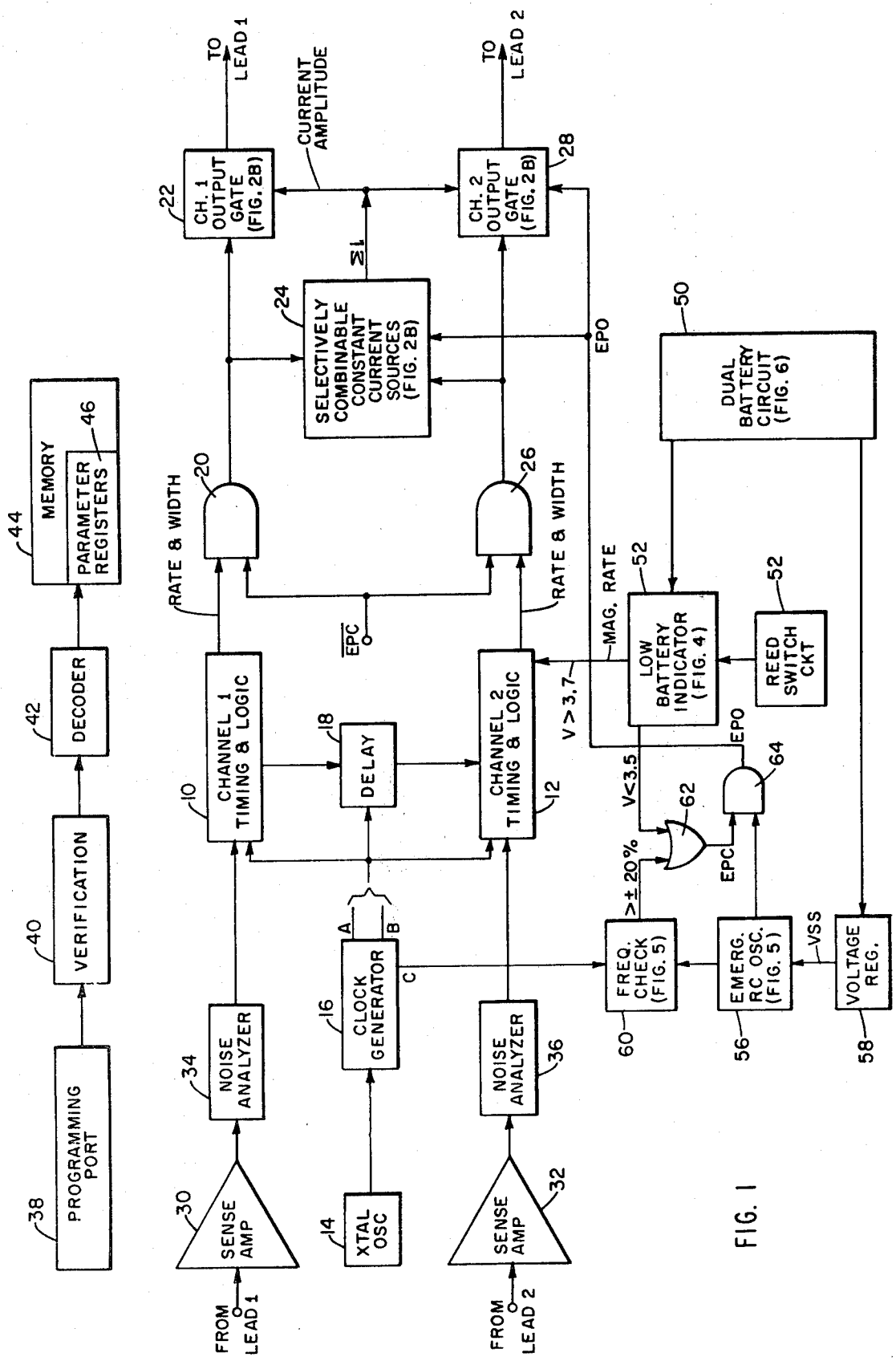
FIG. 1 is a functional block diagram of the overall cardiac pacing system illustrating the interrelationship between the subsystems according to the invention.

FIG. 1 illustrates in funcitonal form the generalized circuit requirements for pacing and programming in an implantable digitally timed multi-mode cardiac pacer having pacer subsystems according to the invention. The electrical components of the pacer are intended to be powered by a set of lithium compound batteries. The components, together with the battery cells, are sealed in the customary biologically compatible hermetic enclosure, such as the "Gamma" TM pacer enclosure manufactured by Cordis Corporation, the assignee of the present application. Much of the circuitry is designed for VLSI C-MOS (very large scale integration complementary metal oxide semiconductor) single chip circuit fabrication techniques. Large components such as capacitors, diodes, resistors and the like are mounted alongside the chip on a common printed circuit board. The disclosure relates to a digitally timed pacing system, and in particular to a prototype pacing system of the microprocessor type under development by Cordis Corporation. However, the inventions to which this application is directed are not necessarily restricted to microprocessor type pacers or even to digitally timed pacers, except where otherwise indicated herein. Indeed, pacing logic for the pacing modes to which the present inventions are applicable is already known and has nothing to do with the specific improvements disclosed herein and to which this application is limited.

The pacer itself is implanted at a suitable location in the human body and is electrically interconnected with a multiconductor pacer lead which terminates in two distal ends for the respective heart chambers. In a conventional unipolar electrode arrangement, the electrically conductive case of the pacer forms the return path or ground electrode. Alternatively, bipolar leads, also known in the art, may be employed with corresponding minor output circuit modifications.

The system of FIG. 1 consists of two main pacing/sensing channels associated with lead 1 and lead 2, respectively, designed to be connected to the right atrium and the right ventricle. Each channel has the functional equivalent of separate timing and logic circuit 10 and 12. The fundamental timing for all of the operations of the timing and logic circuits 10 and 12 is provided by a clock circuit including a crystal oscillator 14 with a nominal frequency of 32.768 kilohertz (kHz). This frequency output is logically manipulated in a clock generator 16 to produce a number of slower regular timing signals A, B and C. Timing signals A and B have periods of 244 and 61 microseconds, while timing signal C has a period of 7.8125 ms in the specific embodiment used by way of example for this disclosure. Timing signal A is produced in eight phases separated by about 30 microseconds. The timing and logic circuits 10 and 12 produce logic outputs at appropriate times during a timing cycle depending on the programmed pacing mode. In certain pacing modes such as AV synchronous and AV sequential, the channel 2 output occurs following a programmable delay shown functionally in FIG. 1 as delay block 18 which also uses the output of the clock generator 16 as its time base. When the timing and logic circuit 10 for channel 1 determines that it is time to stimulate on lead 1 (atrium), a binary signal with a preselected pulse width is applied via an AND gate 20 or the equivalent to the channel 1 output gate 22. The presence of a stimulation signal from the channel 1 gate 20 activates a normally dormant circuit 24 which selectively combines the preselected constant current sources to produce an output pulse via the output gate 22 to lead 1 of the desired current amplitude. The width of the resultant pulse on lead 1 is determined by the width of the binary pulse from the channel 1 gate 20. Similarly, when the timing and logic circuit 12 for channel 2 determines that it is time to issue a stimulation pulse, a binary signal is applied via AND gate 26 to the channel 2 output gate 28 which passes the constant current preselected for channel 2 to lead 2 (ventricle).

To avoid competing with natural heart rhythms, conventional ventricular inhibited or triggered and atrial inhibited or triggered functions are implemented by connecting the inputs of sense amplifiers 30 and 32 to leads 1 and 2 and the outputs to the respective timing and logic circuits 10 and 12 via respective noise analyzer circuits 34 and 36. Noise analyzers 34 and 36 disable the inhibiting inputs to the pacing logic in the presence of electromagnetic interference, thus allowing the pacer to revert to asynchronous pacing at a fixed rate. Variable parameters such as output level, sensitivity of the sense amplifiers, refractory periods, fixed rate, etc. can be programmed externally in a number of known ways. For example, a succession of a particular number of externally generated magnetic impulses at about 300 hertz is used in pacers marketed under the name "Omnicor" TM by the assignee Cordis Corporation. In the pacer of FIG. 1, a magnetic responsive programming port 38, typically comprising a reed switch circuit, produces a binary pulse train representative of the number, width and frequency of pulses transmitted. The pulse signal is passed via a verification circuit 40 to a decoder circuit 42. The information represented by the pulse code is typically stored to the extent necessary in a memory 44 having a plurality of parameter registers 46. The current contents of the parameter registers determines the values of the pacing parameters. The programmed rate code, for example, is employed by the timing and logic circuitry to determine when it is time to stimulate on lead 1, for example, in the AV sequential mode. With the notable exception of the selectively combinable constant current sources 24, the foregoing detailed description applies generally to existing cardiac pacers.

A dual battery circuit 50 is the self-contained power source for all the electronic circuitry in the pacer of FIG. 1. As power is consumed from the battery circuit 50, toward the end of its service lifetime, the voltage level drops from its nominal starting value of 4.2 volts. A low battery indicator circuit 52 samples the battery voltage and compares it to two thresholds, 4.1 volts and 3.9 volts. The battery voltage in relation to the first threshold 4.1 volts can be "read" by the physician by way of the "magnet rate". To initiate this diagnostic mode, the physician places a permanent magnet over the pacer. As in the past, a reed switch in a reed switch circuit 54, closes and remains closed while the permanent magnet is in proximity to the pacer. The reed switch circuit 54 can also serve as the programming port 38. Maintaining the closed condition, the reed switch circuit 54 signals the timing logic for channels 1 and 2 to cease normal operation and to revert instead to a preselected fixed rate mode. Typically, the fixed rate is an asynchronous atrial and ventricular stimulation at about 70 beats per minute. If the low battery indicator 52 indicates that the battery voltage is above 4.1 volts, normal magnet rate operation will be initiated at 70 beats per minute. However, if the battery voltage is below 4.1 volts, the timing and logic circuitry will produce a different fixed rate asynchronous output. To produce a distinctively recognizable change in magnet rate, 62.5 beats per minute has been chosen.

In addition to the main timing and logic circuitry 10 and 12 of channels 1 and 2, the cardiac pacer of FIG. 1 includes a separate backup pulse generator in the form of an emergency RC oscillator 56. The oscillator 56 is powered by the dual battery circuit 50 via a voltage regulator 58. The oscillator circuit 56 produces outputs for two separate functions. First, a reference time base is supplied to a frequency checking circuit 60 which receives timing signal C from the clock generator 16. Second, the oscillator 56 produces an emergency stimulation timing output at the rate of 52.5 pulses per minute with a pulse width of 1 millisecond. Normally, however, this emergency stimulation output is not utilized. Either of two independent events can bring the emergency stimulation output into play. The more important one is the sensing of battery voltage below the second threshold, 3.9 volts, by reason of the normal depletion profile or catastrophic battery failure. The other condition corresponds to failure of the main clock circuit due, for example, to failure of the crystal. This condition is determined by the frequency checking circuit 60 which produces an output signal if it finds that the sample frequency C is more than about 20% different from its nominal frequency. These two hazard signals, low battery and crystal failure are applied via an OR gate 62 or the equivalent whose output EPC, designating the emergency pacing control mode, is fed along with the emergency oscillator output to an AND gate 64 or the equivalent whose output is the emergency pacing output (EPO).

When in the emergency mode, the outputs of the timing and logic circuitry for channels 1 and 2 according to the preprogrammed parameters are disabled by gates 20 and 26. Simultaneously, the 52.5 bpm output is used to drive channel 2, normally connected to the ventricle to provide fixed rate pacing at a unique frequency, i.e., one that differs measurably from programmable rates.

Thus, the fixed rate pacing regime is indicative of three progressively lower voltage ranges. Between 4.1 and 4.2 volts, the magnet rate calls for fixed rate pacing at 70 bpm. Between 3.9 and 4.1 volts, the magnet rate is changed to 62.5 bpm due to the indication from the low battery indicator 52. Below 3.9 volts, battery capacity is seriously depleted and the pacer operates continuously via the emergency oscillator which produces stimulation at 52.5 bpm to sustain life until replacement.

Figure 2A:
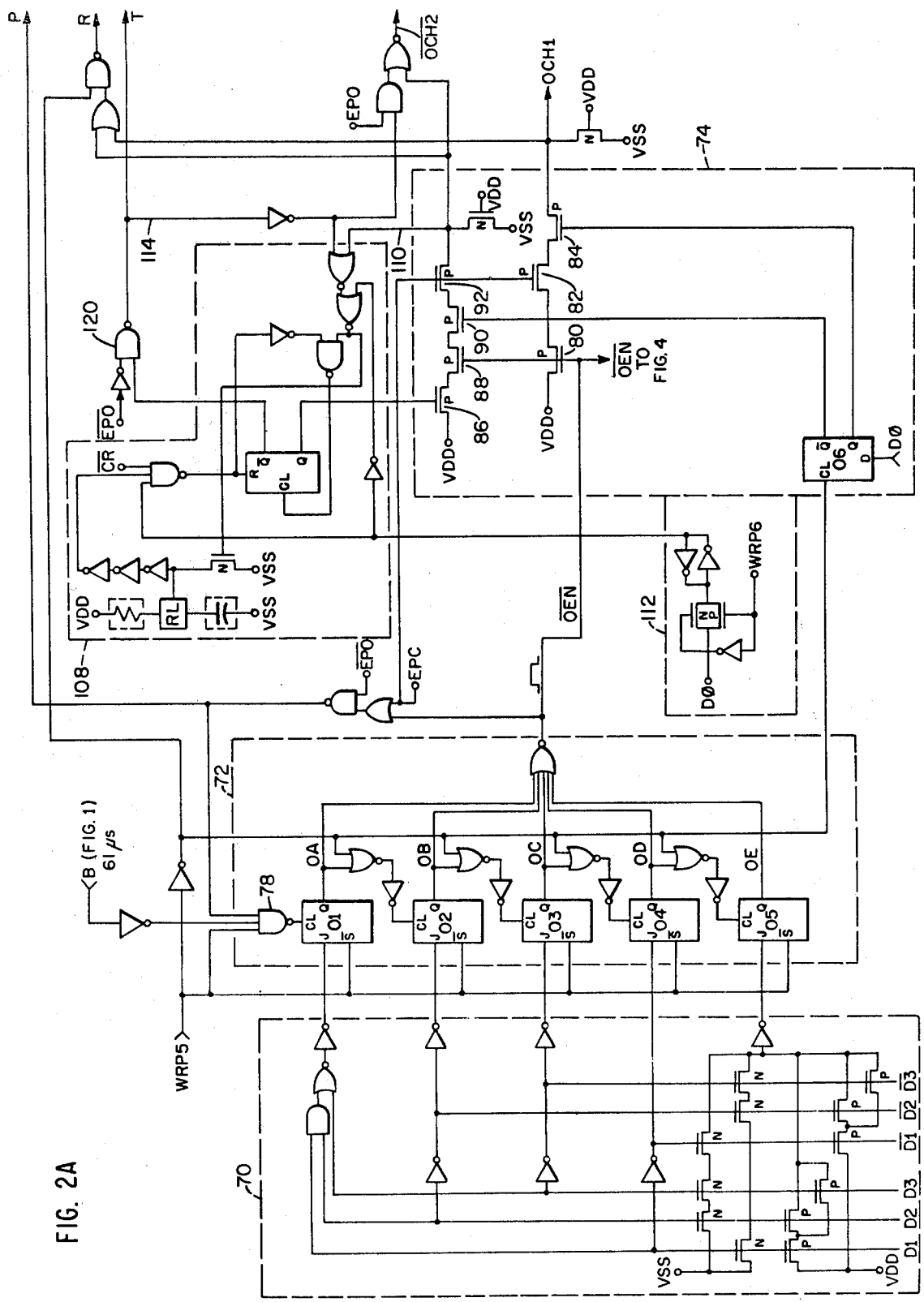
FIGS. 2A and 2B are an electrical schematic drawing of the output circuit of FIG. 1.
Figure 2B:
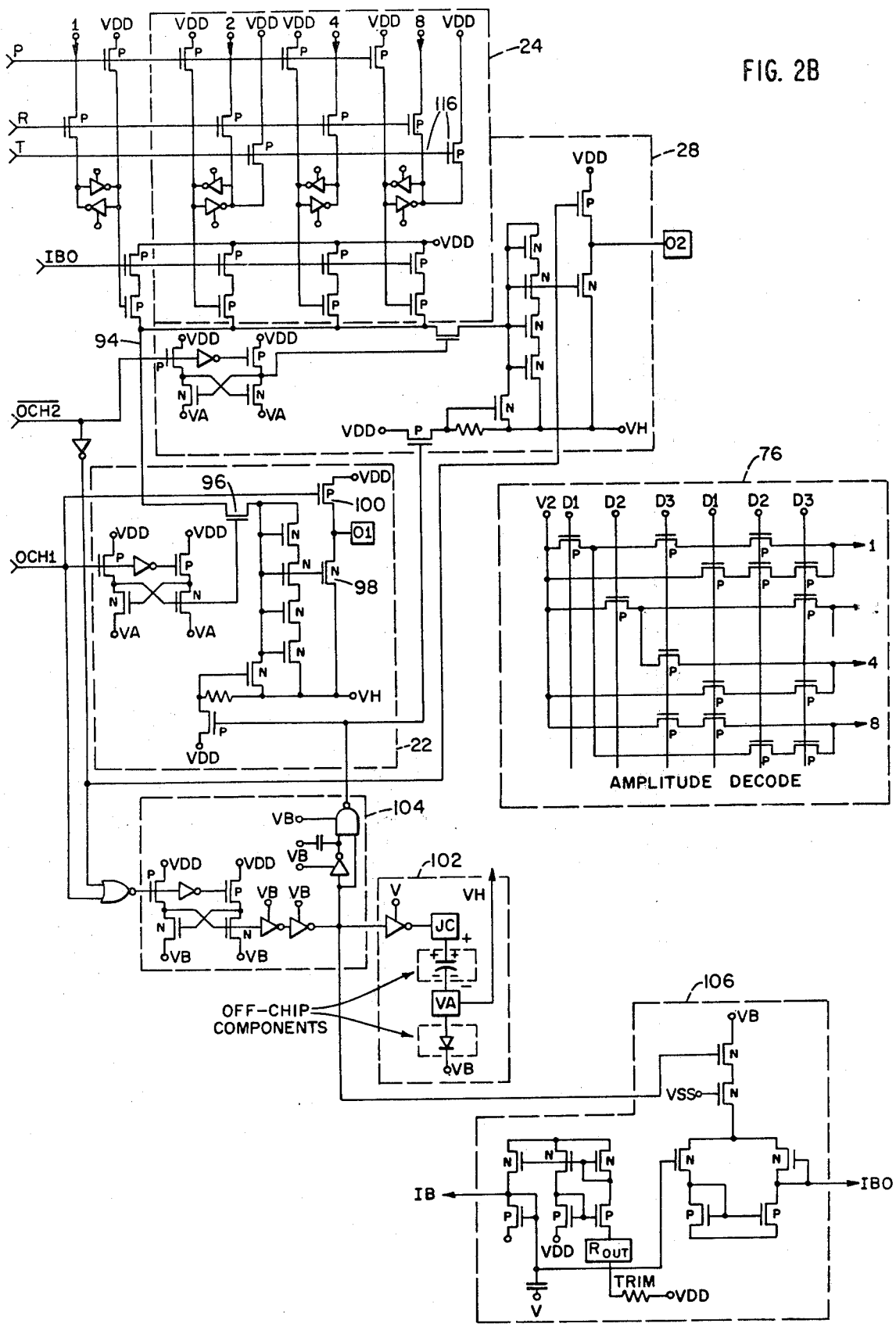
Figure 3A:
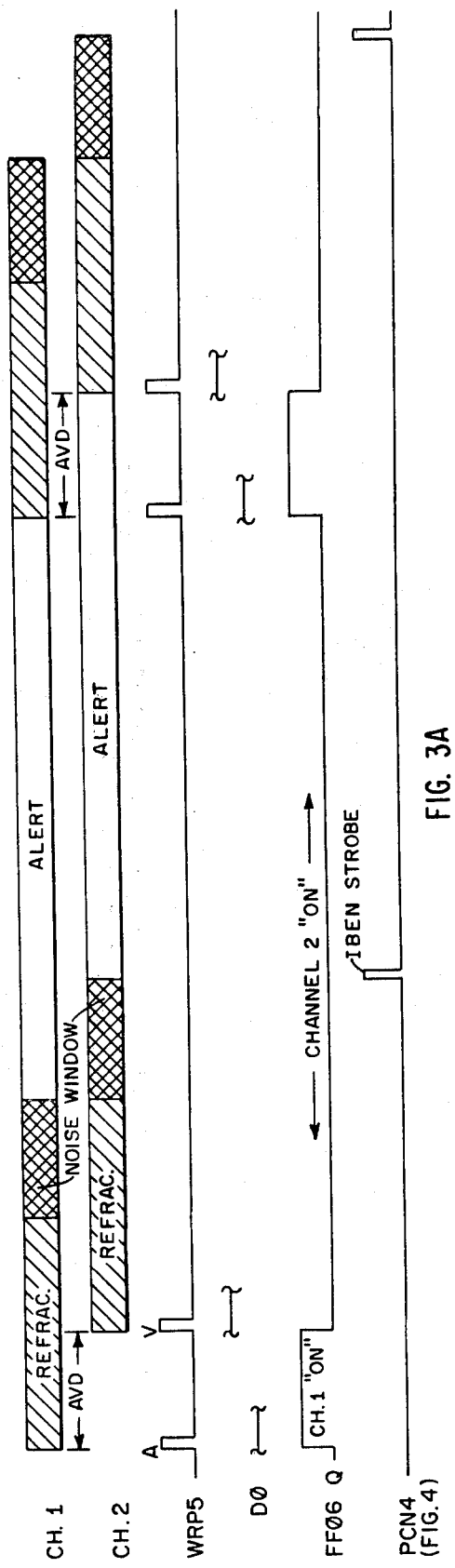
FIGS. 3A and 3B are functional timing diagrams illustrating the relationship between timing signals utilized in circuitry of FIGS. 1, 2 and 4 when the pacer is operating in an AV sequential mode.
Figure 3B:
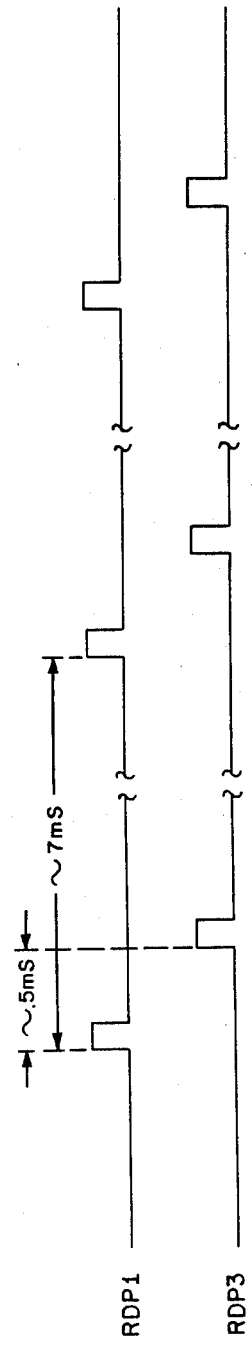
Figure 4:
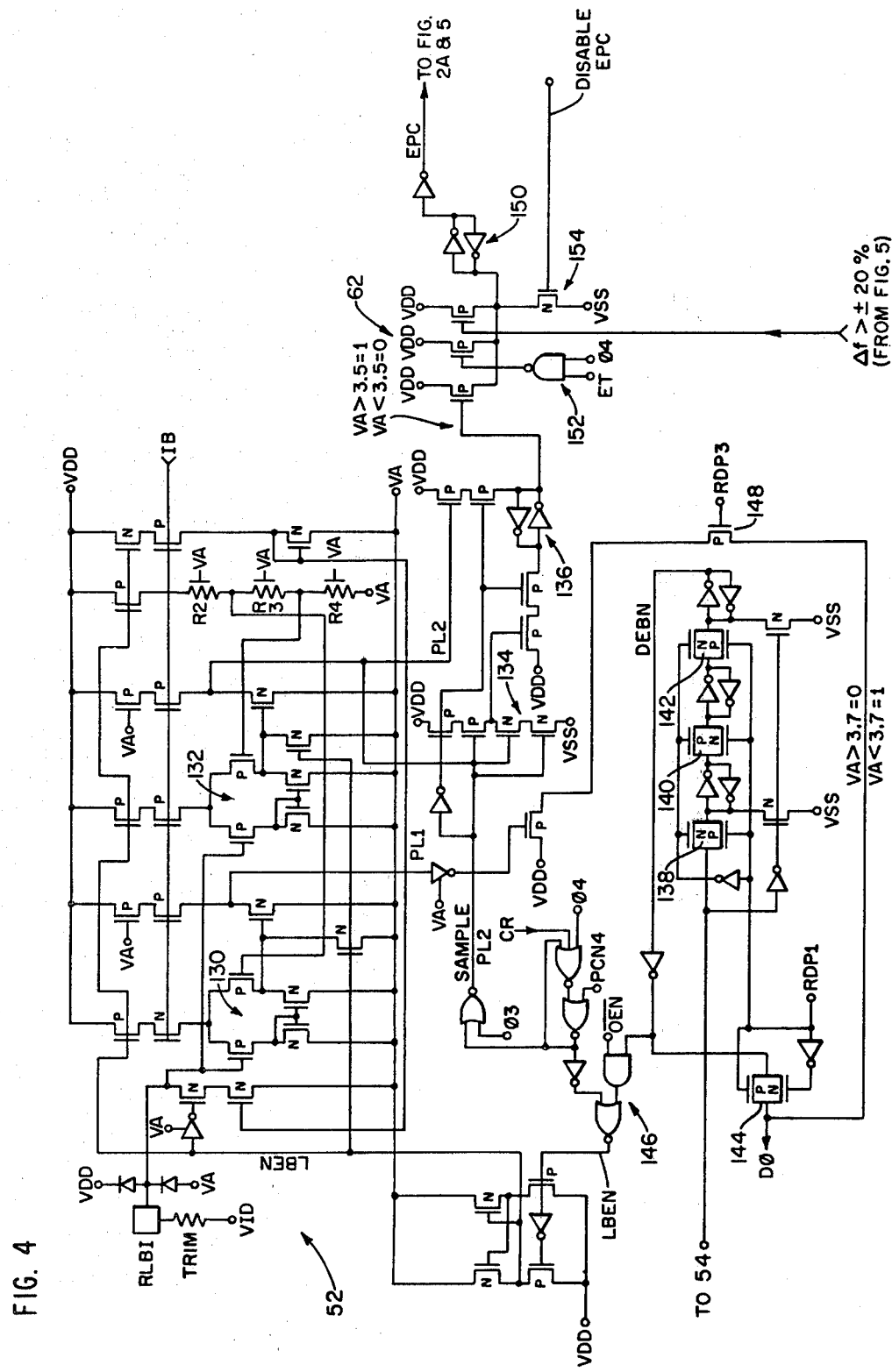
FIG. 4 is an electrical schematic drawing of the low battery indicator circuit of FIG. 1.
Figure 5:
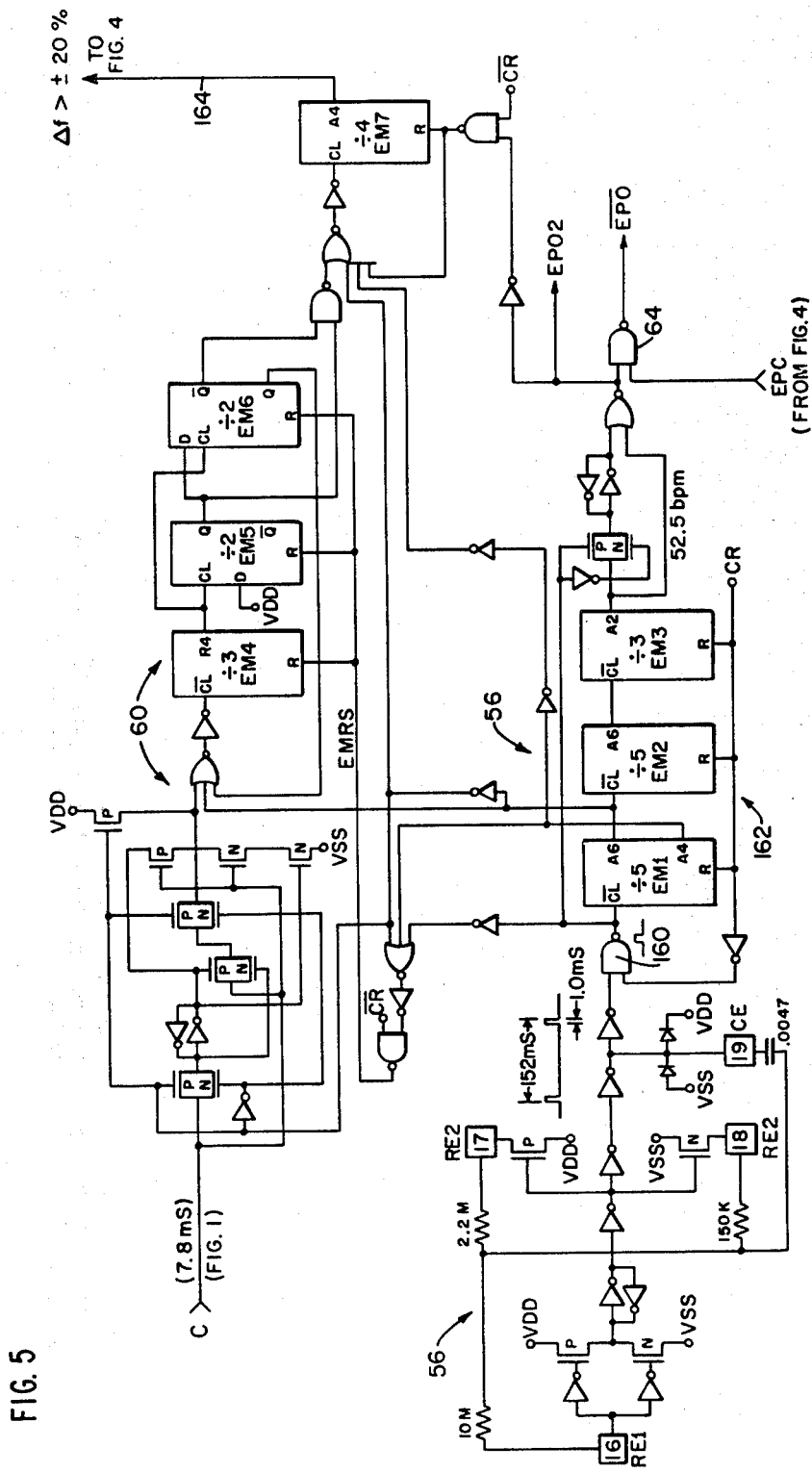
FIG. 5 is an electrical schematic drawing of the emergency oscillator and frequency checking circuits of FIG. 1.

In conjunction with the timing diagrams in FIGS. 3A and 3B, the detailed integrated circuitry for output formation, low battery indication and frequency checking as well as for the emergency RC oscillator, is shown in FIGS. 2, 4 and 5 to illustrate one currently preferred embodiment. The overall pacing system, of which the circuitry of FIGS. 2, 4 and 5 forms a part preferably includes microcomputer-based pacing, programming and telemetry systems which are not germaine to the present application and are therefore omitted. The microcomputer interacts with the circuitry of FIGS. 2, 4 and 5 only to the extent of providing timing and trigger signals, which are fully described below.

The circuit of FIG. 2 is composed in the main of P channel and N channel MOS field effect transistors (FET). The various power supply voltages used throughout this circuitry include VA and VB which are both nominally 4.2 volts relative to ground, VDD. Voltage VSS is a regulated voltage fixed at a particular level between 1.8 and 2 volts. Certain ones of the gate configurations are shown in conventional logic notation such as flip-flops and NOR gates as if they were discrete integrated circuits. Nevertheless, all the circuitry in FIGS. 2, 4 and 5 is designed to be fabricated on a single chip.

The output circuitry of FIG. 2 comes into play only when the pacer is called upon to produce a stimulation pulse. When the pacing logic for either channel determines that the time has come for a stimulation pulse to be applied, a timing pulse as shown in the first waveform diagram at the top of FIG. 3A is applied to an input line arbitrarily designated WRP5 in FIG. 2. This pulse initiates the formation of another pulse of selected pulse width which will operate the output gate for the appropriate output channel. The pulse width forming network includes a pulse width decoder 70 and a pulse width counter circuit 72. The pulse width output designated OEN-bar, indicative of the complement of output enable, is passed to an output channel selection circuit 74 having outputs for either channel designated OCH1 for output on channel 1 and OCH2-bar for output on channel 2. Signal OCH1 actuates the output gate 22 (FIG. 1) which applies the selected constant current level from a selectively combinable constant current source 24 to pad 01 which is connectable to lead 1. Similarly, signal OCH2-bar actuates output gate 28 for channel 2.

The constant current source 24 includes four separate current sources for one milliamp, two milliamps, four milliamps and eight milliamps. These are combined according to the outputs of an amplitude decoder circuit 76. The pulse width and amplitude decoder networks 70 and 76 decode three bits D1, D2 and D3. The eight permutations of these three bits are used to define paired combinations of pulse width and current amplitude in accordance with the following table.

ergy increases over a wide range as programmed amplitude increases. In the table the $D_0$ bit represents a binary indication of the channel. When $D_o$ is "1", the pulse width and amplitude for channel 2 are simultaneously determined by the present binary values of bits D1, D2, and D3. When $D_0$ is "0", the duration and current amplitude of a stimulation pulse on channel 1 is determined simultaneously by the present values of bits D1, D2, and D3. These four D bits represent a data bus which would be connected, for example, between a central processing unit and a random access memory corresponding to the parameter registers 46 in FIG. 1. Thus, when the pacing logic determines that it is time to apply a stimulation pulse to channel 2, the $D_0$ bit of the data bus goes high and the three bit pulse width/amplitude code for channel 2 is placed on the remaining respective bit lines of the data bus. Conversely, if the pacing logic determined that it was time for an output pulse on channel 1, the $D_0$ bit of the data bus would go low and the pulse width/amplitude code for channel 1 would be taken from memory and placed on the remaining respective bits of the data bus.

The operation of the pulse width forming circuit 70 and 72 and the current amplitude forming circuits 76 and 24 is independent of the selected channel and therefore the corresponding circuitry is common to both channels. The pulse width forming circuit 72 includes five flip-flops in a counting chain. The first flip-flop is clocked in accordance with the B timing signal via gate 78 which is enabled by the pulse initiation signal on line WRP5. The counting chain in circuit 72 is enabled for long enough to count up to the maximum pulse width for approximately 2 milliseconds. The Q outputs of the five flip-flops in circuit 72 are combined in a NOR gate to produce the OEN-bar output to the channel selection circuit 74.

Channel 1 in the channel selection circuit 74 has three serially connected P channel MOS FET's or gates 80, 82 and 84, all of which must be conducting or "closed" in order to produce an output on channel 1. Channel 2 in the channel selection circuit 74 has four series connected P channel gates 86, 88, 90 and 92 which must be similarly conducting in order to produce a stimulation output on channel 2. Flip-flop 06 of circuit 74 selects the appropriate channel via gates 84 and 90 connected respectively to the complementary outputs of the flip-flop. For example, in AV sequential operation, flip-flop 06 would alternate the channels. The data input is connected to the $D_0$ bit of the data bus and the clock input of the flip-flop is operated by the complement of line WRP5, the pulse initiation signal line. As shown in the

TABLE I

| PROGRAM DATA BUS | | | | OUTPUT PORT (FIG. 2) | | | | | | |
|---|---|---|---|---|---|---|---|---|---|---|
| $D_3$ | $D_2$ | $D_1$ | $D_0$ | OE | OD | OC | OB | OA | P.W. | AMP. |
| 0 | 1 | 1 | x | 0 | 0 | 0 | 1 | 1 | .2 ms. | 2.0 ma. |
| 1 | 0 | 1 | x | 0 | 0 | 1 | 0 | 1 | .3 ms. | 3.0 ma. |
| 1 | 1 | 1 | x | 0 | 0 | 1 | 1 | 1 | .4 ms. | 4.0 ma. |
| 0 | 0 | 0 | x | 0 | 1 | 0 | 0 | 0 | .5 ms. | 5.0 ma. |
| 0 | 1 | 0 | x | 0 | 1 | 0 | 1 | 0 | .6 ms. | 6.0 ma. |
| 1 | 0 | 0 | x | 0 | 1 | 1 | 0 | 1 | .8 ms. | 8.0 ma. |
| 0 | 0 | 1 | x | 1 | 0 | 0 | 0 | 0 | 1.0 ms. | 10.0 ma. |
| 1 | 1 | 0 | x | 1 | 1 | 1 | 1 | 1 | 2.0 ms. | 12.0 ma. |

$D_0 = 1 = $ CH.2
$D_0 = 0 = $ CH.1

This system links pulse duration with amplitude so that programmed amplitude can be determined by observation of pulse width on an oscilloscope. The output entiming diagram of FIG. 3A, the "0" or "1" condition of data bit $D_0$, sampled when a stimulation initiation pulse arrives on WRP5, selects the appropriate one of the Q and Q-bar outputs. The out-put pulse width signal OEN-bar from pulse width circuit 72 is applied simultaneously to gates 80 and 88 in channel 1 and channel 2 respectively. Gates 82 and 92 have to do with the emergency mode and are normally closed. Thus when an output pulse appears for channel 1, gates 80, 82 and 84 are closed causing line OCH1 to go high which actuates the output gate circuit 22.

Constant current amplitude control is supplied via common line 94 to the identical output gate circuits 22 and 28 for channels 1 and 2. The parallel current sources are tied together in line 94 so as to sum the selected currents to produce the amplitude called for by the pulse width/amplitude code. Signal OCH1 causes the selected current amplitude to be switched through P channel gate 96 to terminal VH also causing a large N channel gate 98 having an "on" resistance of approximately 40 ohms to be closed. The series P channel gate 100 is normally closed and is used to discharge the output capacitor (not shown) after a pulse is applied. Thus gate 100 is tied to OCH1 for complementary action with respect to the N channel gate 98.

The gates 98 and 100 are connected between VDD and a special voltage VH produced by a voltage doubler circuit 102. Since the voltage doubler would draw current when not in use, a voltage doubler switching circuit 104 is operated in accordance with the channel 1 and channel 2 output signals. Without the voltage doubler circuit, it would not be possible to get 4.2 volts to drive more than 8 milliamps into the 500 ohm load seen by the output terminal. The output of the switching circuit 104 also drives a constant current source 106 which provides a voltage reference IBO to the current source circuit 24 in order to calibrate the current amplitude. Pad R-OUT in circuit 106 is connected via a trim resistor to VDD. During manufacture this resistor is trimmed to produce the correct output level. The trimmed reference level IB is produced constantly and is amplified to produce IBO whenever needed.

The operation of channel 2 is identical to that of channel 1 in normal operation. However, there are two additional functions implemented in connection with channel 2. First, a rate limit circuit 108 includes an RC timed one-shot whose Q output drives the P channel gate 86. The one-shot is triggered via line 110 tied to the channel 2 output line. Thus when channel 2 provides stimulation it also starts a delay in the rate limit circuit 108. This delay is designed to be approximately 333 milliseconds to correspond to the maximum rate of about 180 bpm. Thus immediately following the stimulation pulse a 333 millisecond delay is initiated during which gate 86 is open. Another pulse on channel 2 cannot be initiated until gate 86 closes 300 milliseconds later thus effecting a rate limit function. Latch circuit 112 provides a means for disabling rate limit by software control if desired. When WRP6 goes high, the transmission gate samples $D_0$ which if high sets the Schmitt trigger latch to lock out the one-shot circuit 108.

The other distinctive function for channel 2 occurs during the emergency mode signified by EPC. When battery voltage is below 3.9 or a crystal failure occurs, EPC goes high and opens gate 82 and 92 thus disabling the normal operation of the output channels. The first emergency oscillator pulse selects the 2 milliamp and 8 milliamp constant current sources via dedicated P channel gates 116 and 118 and initiates pulse formation via the OCH2-bar line as well as a rate limit via line 114.

The rate limit output is connected in this instance to gate the amplitude selection line off via gate 120 for 300 milliseconds following an emergency oscillator pulse. The remainder of the operation of the output circuit for channel 2 in the emergency mode is the same as in the normal mode.

In connection with the output current circuit 24, it should be noted that the constant current circuits are enabled only when actually needed. This is accomplished by gating the ground connection VDD for each individual circuit "off" in the absence of an output enable pulse or the emergency mode. In addition, the individual amplitude lines 1, 2, 4 and 8 are sampled only during the output command to channel 1 and channel 2.

The purpose of the low battery indicator circuit shown in FIG. 4, is to compare unregulated voltage VA to thresholds corresponding to 4.1 and 3.9 volts. The comparator located at 130 in FIG. 4 corresponds to the 4.1 volt threshold and its determination is indicated by the condition of line PL1 (first plateau). The second comparator 132 provides an output indication on line PL2. Line IB in FIG. 4 comes from the trim circuit 106 for calibrating the output in FIG. 2. The three resistor voltage divider in FIG. 4 provides taps for the two-level voltage comparison. Pad RLBI is connected to VDD via an off-chip trim resistor which adjusts the thresholds.

The low battery indicator circuit 52 draws current and does not have to be on continuously. Therefore, it may be sampled once per pacing timing cycle. Since the output pulse causes a dip in the battery voltage, the ideal point for sampling battery voltage would be somewhere between consecutive output pulses. A convenient timing signal is provided by a signal indicating the end of the noise window, as shown in FIG. 3A. In each channel when a stimulation pulse is issued, a preselected programmable refractory period of approximately 300 milliseconds is begun. The last 100 milliseconds of the refractory period can be used as a noise window. In AV sequential operation, the end of the noise window on the second channel comes about at the midpoint between output pulses and is thus an ideal candidate although an arbitrary choice.

The PCN4 line corresponds to the end of the noise window as shown in FIG. 3A and is used to initiate battery sampling. The clock generator 16 at line A (FIG. 1) produces a 244 microsecond period 8-phase clock signal. Phase 4 of this signal, for example, is used to sample PL2. The sample gate actuates a transmission gate comprised of the two outside P and N channel gates in the four gate chain at 134 in FIG. 4. The inner two transistors invert PL2 which is latched at 136 to provide a logic signal to an OR gate equivalent network 62. In the event that the PL2 threshold has been crossed and the voltage is below 3.9 volts, the EPC line goes high indicating the start of the emergency mode.

PL1 is sampled in a different way as it relates to the magnet rate. As shown in FIG. 3B, once every 7 milliseconds for an arbitrary example, a pulse appears on line RDP1. In FIG. 4 this pulse closes transmission gates 138, 140 and 142 in order to sample the reed switch circuit 54 (FIG. 1). If after three sample pulses, the reed switch is still on, the diagnostic enable line DEBN goes high indicating that a permanent magnet has been applied. This information is passed during RDP1 via transmission gate 144 to the data bus $D_0$ or the equivalent in order to indicate to the pacing logic that the magnet rate should begin. Line DEBN also serves to enable the low battery indicator via gates 146. This enablement, however, is gated off whenever an output pulse is enabled to avoid sampling when the battery voltage is distorted by the production of an output pulse.

Following RDP1, as shown in FIG. 3B, in the magnet-accessed diagnostic mode, arbitrarily about 500 microseconds later a pulse appears on line RDP3 which closes gate 148 in order to sample line PL1. PL1 is sampled only when the magnet is in position. The battery indicator circuit 52 also remains enabled via the latched DEBN line while the magnet is in position. As shown in FIG. 4, the high or low condition of PL1 is applied to the data bus bit $D_0$ for testing by software. Alternatively, the condition of PL1 may be supplied to a different output line. In any event, the effect is to tell the pacing logic whether or not the voltage is above or below 4.1 volts. If the voltage is above, then the magnet rate is 70 bpm and if below the rate is 62.5 bpm. The different rates are accomplished in software, for example, by addressing and obtaining the preselected corresponding rate from memory and placing a corresponding number in a regularly incremented rate register.

The OR gate configuration 62 (compare FIG. 1) produces the emergency mode output EPC whenever latch 136 corresponding to the sampled condition of line PL2 indicates that battery voltage is below 3.9 volts. OR gate 62 also includes a latch 150 which keeps EPC at the emergency mode level once it is triggered by low battery voltage or false frequency. Gate 152 provides a test input for the emergency mode via line ET. In normal operation, once the emergency mode has begun it cannot be exited. However, gate 154 provides a means for disabling the emergency mode. If desired, a software command can be issued to momentarily apply VSS to the latch 150 thus switching its state to the nonemergency mode.

In FIG. 5, the emergency oscillator 56 occupying the lower half of the drawing includes an RC oscillator producing an output at gate 160 of about 15.2 milliseconds with a 1 millisecond pulse width. The external components connected to pads 16, 17, 18 and 19 are large off-chip circuit elements and they all have their opposite ends connected together to a common floating point. The 2.2 megohm resistor and 0.0047 microfarad capacitor account for the period of the pulse signal while the 150 kilohm resistor and the same capacitor time pulse width. The 15 millisecond signal is passed to a divide by 75 circuit 162 whose output has a 1 millisecond pulse width and a period of 1.14 seconds at 52.5 pulses per minute.

In addition to forming the emergency pacer output time base, the oscillator 56 provides a reference time base to the frequency checking circuits 60, as shown in FIG. 5. The 7.8 millisecond timing signal C is passed via a transmission gate which is toggled at the rate of 13.2 hertz in accordance with the RC oscillator output. The remainder of the circuitry for the frequency checking function in FIG. 5 accomplishes the net result of producing a binary output on line 164 (A4-bar output of divide-by-4 counter EM7). Line 164 remains low when timing signal C is found to be approximately 7.8 milliseconds. Circuit 60 is designed to produce a low output on line 164 whenever the period of timing signal C exceeds 10.13 milliseconds or falls short of 6.07 milliseconds. This wide tolerance provides adequately for drift of the RC oscillator while insuring that the frequency checking circuit 60 will detect gross frequency changes due to crystal failure. In fact, minor frequency variations within plus or minus 20% are extremely rare for crystal oscillators. Instead, when one does fail, the output goes to zero or to an integral multiple of the nominal frequency (i.e. the period either becomes infinite or drops to at least half the nominal period, e.g., 3.9 ms).

The AND function 64 of FIG. 1 is performed by the corresponding NAND gate in the circuit of FIG. 5 which receives the 52.5 ppm output of the RC oscillator and the emergency mode signal EPC from the OR gate 62 of FIG. 4. As discussed previously in connection with FIG. 2, emergency mode takes control of the output circuit by disabling normal operation of the pacer. The EPO signal forces the current source circuit 24 to produce 10 milliamps and actuates the output gate circuit 28 for channel 2 to apply a 52.5 bpm fixed rate signal on lead 2 with a pulse width of 1 millisecond and a current amplitude of 10 milliamps.

The emergency oscillator 56 is sensitive to the voltage level remaining in the battery circuit 50. For this reason, to minimize drift in the frequency of the output signal, the emergency oscillator is powered by the regulated voltage VSS.

Figure 6:
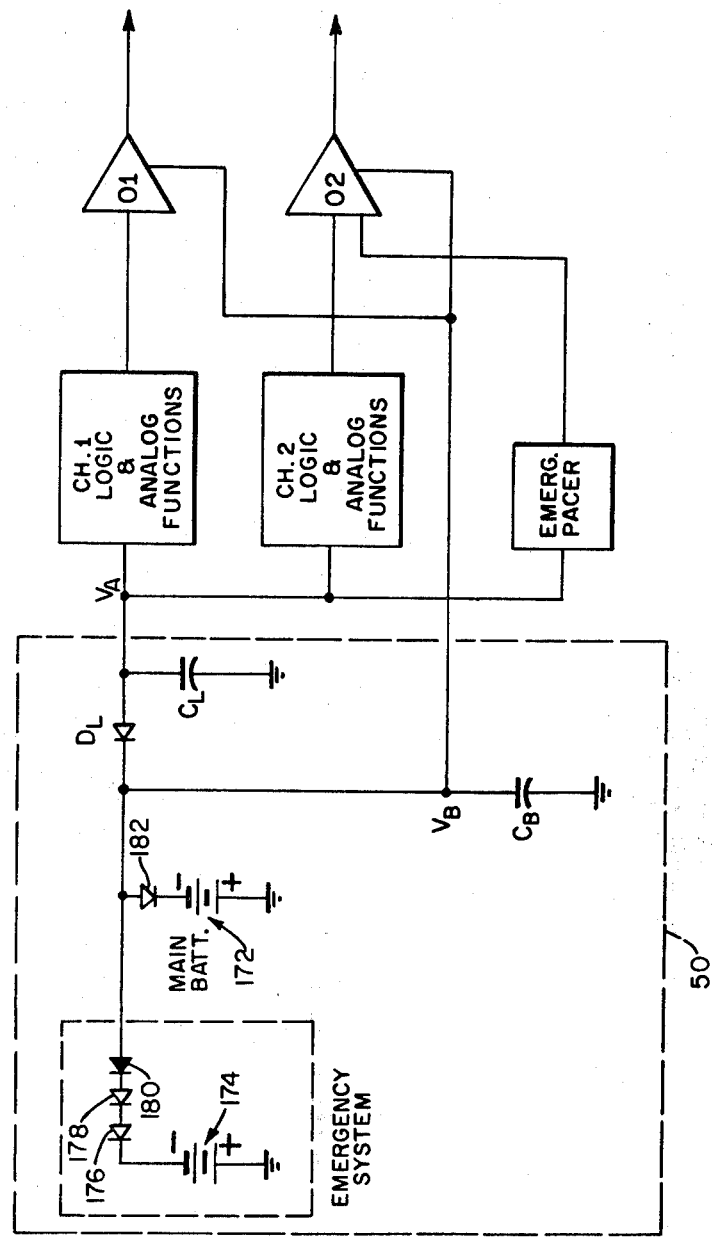
FIG. 6 is an electrical schematic and block diagram of the battery circuit of FIG. 1.

As shown in FIG. 6, the battery circuit 50 has a main battery 172 and an emergency battery 174. Each battery comprises two lithium cupric sulfide cells connected in series. The main battery 172 has a nominal capacity of 1800 milliampere-hours and the emergency battery has a nominal capacity of 125 milliampere hours. Both batteries provide 4.26 volts (nominally) at the beginning of battery life (i.e. 2.13 volts per cell). After about 90% of the battery capacity is discharged, each cell drops to a second stable voltage plateau (1.7 volts) until it is depleted. The output voltage remains sufficiently high however due to the voltage doubler circuit 102 (FIG. 2).

The cathodes of the main and emergency batteries 172 and 174 are interconnected via a set of three series connected diodes 176, 178 and 180. Diode 176 is a Shottky diode. Diodes 178 and 180 are bipolar diodes. The total voltage drop across the three diodes is between 0.6 and 1.4 volt.

Battery capacitor CB and logic capacitor CL are connected to ground in parallel with batteries 172 and 174 separated by a Shottky diode DL. The voltage at the junction of diode DL and capacitor CL is designated VA while the voltage at the junction of diode DL and capacitor CB (i.e., the battery terminal) is designated VB.

As shown in FIG. 6, voltage VB operates the output circuit. With reference to FIG. 2, the voltage VB is employed in circuits 102, 104 and 106 to power the output stages for both channels. Voltage VA is used for the pacing logic. The regulated voltage VSS for the emergency oscillator is derived from voltage VA. In this way, the power supply to the logic circuitry is isolated from the power supply to the voltage doubler output amplifiers. If telemetry were offered by a particular pacer design, the VB voltage would be used for the telemetry output as well.

This arrangement allows considerable depletion of the battery capacitor CB during output without affecting the operation of the pacer logic circuitry. Diode DL isolates the logic power supply from the main battery while capacitor CL maintains the voltage to the logic if the battery voltage drops during an output. Capacitor CL must be large enough to supply enough current to run the logic circuitry, in this case approximately six microamps, without a significant drop in voltage when the main battery is low from the effects of a large output pulse. A worst case analysis indicates that a value of one microfarad for capacitor CL is sufficient to maintain a constant voltage.

When a large output pulse (or a complete telemetry dump, if available) occurs, the current demand cannot be immediately supplied by the main battery due to its inherent internal impedance. Accordingly, a portion of the required current is derived from the charge stored in the battery capacitor CB. The voltage doubler capacitor in circuit 102 (FIG. 2) is effectively in series with CB at the moment an output pulse occurs and both capacitors experience a reduction in voltage as a result of their charge depletion. Since the logic circuits are supplied from the decoupled power source (VA), their input voltage level will remain nearly constant during this drop in the main battery voltage. After an output, capacitor CB and the voltage doubler capacitor will recharge. For a maximum battery impedance of 1000 ohms and a total capacity of 44 microfarads, the charging time constant is 44 milliseconds.

Previous battery connection schemes without isolation of the logic and output power supplies required very large output capacitors so that only a small percentage of the charge from the battery capacitor would be used. With the circuit of FIG. 6, a much larger percentage of the capacitor charge may be removed and thus a smaller capacitor value can be used for CB. As the output capacitor forms one of the largest discrete components of the pacer, any reduction in size is a significant advantage.

The emergency battery system comprising emergency battery 174 and diodes 176, 178 and 180 supplies current to the pacer whenever the main battery voltage falls below a level of about 3.9 volts. During large outputs, voltage VB may drop more than 0.7 volts from its nominal value and some current will be drawn at that time from the emergency battery.

Across each diode, there is a characteristic fixed voltage drop in the forward-biased condition. When conducting, the Shottky diode 176 has a drop of about 0.2 volt while the silicon bipolar diodes 178 and 180 exhibit a larger drop of about 0.6 volt. The objective is to have a well defined transition point so that the emergency battery will come on line at about the same voltage as that associated with PL2, namely 3.9 volts. This feature insures a coordinated transition to emergency battery and emergency mode pacing via independent switching circuitry. Shottky diodes have a more sharply defined cut-off characteristic but exhibit such a low forward drop that it would take several more than two of them in series to switch the emergency battery in at the desired voltage point. Thus a combination of Shottky and bipolar diodes is used to achieve the desired function with fewer discrete parts.

Shottky diode 182 is connected in series with the main battery to protect the emergency battery from being pulled down or discharged in the event of a direct short in the main battery 172. The likelihood of such a short is extremely remote and if one did occur it would probably be a relatively high impedance short. Thus, since diode 182 does lower the voltage VB available to the output circuit by 0.2 to 0.3 volt, diode 182 is a very conservative option which might be dispensed with in an appropriate case.

The above-described cardiac pacer subsystems define specific improvements in the areas of power supply, output circuitry, current amplitude and pulse width determination and response to the emergency condition of crystal oscillator failure as well as low battery voltage. The system provides the physician with a means of determining the intensity of the stimulation pulse by observing a fast oscilloscope trace to gauge the width of the output pulse, from which the exact current amplitude can be ascertained. In addition, the physician is provided with three fixed rate stimulation modes which indicate the condition of the pacer so that appropriate action can be planned. The emergency pacer rate of 52.5 bpm is low enough to be noticeable to the patient in order to alert him to the need for immediate replacement. The emergency oscillator and emergency battery provide a backup system which in a real sense represents an extra pacer combined with the main pacer in one package. While lacking programmability and other functions of the main pacing system in this embodiment, the emergency pacer system has the advantage of avoiding all of the circuitry of the main pacer except for the output circuit. Moreover, the switching in of the emergency battery is implemented by passive circuitry separate from the low battery indicator. Together with the advantage of RC reliability, the emergency backup system as a whole provides both physician and patient with a new degree of confidence in the reliability of the pacer. Moreover, all of the circuitry described herein with few exceptions is suitable for very large scale integration on a single chip to facilitate further miniaturization of the pacer.

Many variations and substitutions may be made in the above described circuitry consistent with the fundamental principles of the invention. For example, the output of the low battery indicator circuit can be used by software to effect other changes in the main pacing routine. Although designed to accommodate software-based digital pacers, the circuitry may be adapted for use with a variety of discrete digital, software-based or analog-timed tissue stimulators, where applicable. Various features disclosed above may be used separately. For example, the emergency battery system is applicable independent of the low battery indicator system or the paired amplitude/pulse width code system.

Accordingly, as various changes can be made in the above construction without departing from the spirit or scope of the invention, it should be understood that all matter contained in the above description or shown in the accompanying drawing shall be interpreted as illustrative and not in a limiting sense.

What is claimed is:

1. An implantable externally programmable tissue stimulator having output means for producing electrical stimulation pulses on command on a lead, a plurality of parameter registers for storing selected externally programmable parameter values including rate and pulse intensity, stimulating logic means for causing said output means to produce a stimulation pulse in accordance with a stored rate value and means in said output means for determining the pulse intensity in accordance with the stored intensity value, wherein the improvement comprises register means among said parameter registers for storing a single selected numerical value indicative of a corresponding one of a known set of preestablished uniquely paired combinations of differing pulse duration and amplitude for the electrical stimulation pulses, and means in said output means responsive to said selected value and said stimulating logic means for forming an output stimulation pulse with a duration and amplitude corresponding to the paired combination indicated by said selected value stored in said register means.

2. The stimulator of claim 1, wherein said pulse forming means includes a pulse width forming circuit means responsive to said selected value and said stimulating logic output for issuing a binary pulse with a duration corresponding to the stored selected value, and a separate amplitude selection means coupled to said lead responsive to said binary pulse and said selected value for producing an electrical output stimulation pulse with an amplitude corresponding to said stored selected value for a period corresponding to the duration of said binary pulse.

3. The stimulator of claim 2, wherein said amplitude selection means includes a plurality of means for producing different constant currents, means for combining selected ones of said means for producing different constant currents in accordance with said stored selected value to establish a corresponding current amplitude for said output stimulation pulse.

4. An implantable externally programmable tissue stimulator having two output channels for connection to separate leads, stimulating logic means for providing a pulse to cause stimulation via one or the other of said output channels, parameter registers for storing externally programmable values indicative of rate and pulse intensity, wherein the improvement comprises first and second pulse intensity register means among said parameter registers corresponding to said first and second output channels each for storing a single selected value indicative of a corresponding one of a known set of preestablished uniquely paired combinations of differing pulse duration and amplitude for stimulation pulses for the respective output channel, means for indicating whether said first channel or said second channel is to be stimulated, and a single pulse width forming circuit means responsive to said stimulating logic output for issuing a binary pulse with a duration corresponding to the stored selected value for the channel indicated by said indicating means, and a single separate amplitude selection circuit means for producing for the channel indicated by said indicating means an electrical stimulation pulse with an amplitude corresponding to the stored selected value for the channel indicated by said indicating means for a period corresponding to the duration of said binary pulse.

* * * * *